(12) United States Patent
Gilmore et al.

(10) Patent No.: US 11,125,796 B2
(45) Date of Patent: Sep. 21, 2021

(54) ELECTROMAGNETIC IMAGING AND INVERSION OF SIMPLE PARAMETERS IN STORAGE BINS

(71) Applicants: 151 Research Inc, Winnipeg (CA); University of Manitoba, Winnipeg (CA)

(72) Inventors: Colin Gerald Gilmore, Winnipeg (CA); Ian Jeffrey, Winnipeg (CA); Joe LoVetri, Winnipeg (CA); Mohammad Asefi, Winnipeg (CA); Nicholas Geddert, Winnipeg (CA); Kevin Brown, Winnipeg (CA)

(73) Assignees: University of Manitoba, Winnipeg (CA); 151 Research Inc., Winnipeg (CA)

( * ) Notice: Subject to any disclaimer, the term of this patent is extended or adjusted under 35 U.S.C. 154(b) by 0 days.

(21) Appl. No.: 16/920,212

(22) Filed: Jul. 2, 2020

(65) Prior Publication Data
US 2021/0003621 A1 Jan. 7, 2021

Related U.S. Application Data

(60) Provisional application No. 62/912,337, filed on Oct. 8, 2019, provisional application No. 62/892,136, filed
(Continued)

(51) Int. Cl.
*G01R 27/28* (2006.01)
*G01F 22/00* (2006.01)
(Continued)

(52) U.S. Cl.
CPC ............. *G01R 27/28* (2013.01); *G01F 22/00* (2013.01); *G01N 22/00* (2013.01); *G01R 27/02* (2013.01);
(Continued)

(58) Field of Classification Search
CPC ...... G01R 27/28; G01R 35/005; G01R 27/32; G01R 27/02; G01R 27/04; G01R 27/16;
(Continued)

(56) References Cited

U.S. PATENT DOCUMENTS

| | | | | |
|---|---|---|---|---|
| 2013/0170569 A1* | 7/2013 | Karabinis | ............... | H04B 7/068 375/260 |
| 2015/0055729 A1* | 2/2015 | Karabinis | ................ | H04B 1/04 375/295 |

(Continued)

OTHER PUBLICATIONS

Gilmore, Asefi, Paliwal, Lovetri, "Industrial Scale Electromagnetic Grain Bin Monitoring", Published in Computers and Electronics in Agriculture, 136, 210-220 (2017).
(Continued)

*Primary Examiner* — Raul J Rios Russo

(57) ABSTRACT

A method for electromagnetic imaging of containers receives uncalibrated first data corresponding to signals of a first plurality of different frequencies associated with an antenna array residing in a container having contents. The method estimates of a second data based on a computer model and simulation of signals of a second plurality of different frequencies associated with the antenna array, the second plurality of different frequencies including a subset of the first plurality of different frequencies. The method compares magnitudes, without corresponding phase comparisons, of the first and second data at each frequency of the second plurality of different frequencies. The method updates the second data based on the comparing. The method provides information about the contents within the container based on the updated second data.

14 Claims, 13 Drawing Sheets

Related U.S. Application Data on Aug. 27, 2019, provisional application No. 62/870,251, filed on Jul. 3, 2019.

(51) Int. Cl.

| | | |
|---|---|---|
| *G01N 22/00* | (2006.01) | |
| *G01R 35/00* | (2006.01) | |
| *G01R 27/32* | (2006.01) | |
| *G01R 27/02* | (2006.01) | |
| *G01R 27/04* | (2006.01) | |
| *G01R 27/16* | (2006.01) | |
| *G01R 31/28* | (2006.01) | |
| *G01R 23/20* | (2006.01) | |

(52) U.S. Cl.
CPC ............. *G01R 27/04* (2013.01); *G01R 27/16* (2013.01); *G01R 27/32* (2013.01); *G01R 35/005* (2013.01); *G01R 23/20* (2013.01); *G01R 31/2822* (2013.01)

(58) Field of Classification Search
CPC ..... G01R 31/2822; G01R 23/20; G01F 22/00; G01N 22/00; G01N 33/0098; G01N 22/04; G01N 33/025
USPC .......... 324/76.11–76.83, 459, 600, 615, 638, 324/649, 650

See application file for complete search history.

(56) References Cited

U.S. PATENT DOCUMENTS

| | | |
|---|---|---|
| 2017/0199134 A1 | 7/2017 | Lovetri et al. |
| 2017/0212210 A1* | 7/2017 | Chen .......................... G01S 5/06 |
| 2019/0056258 A1 | 2/2019 | Gelada Camps et al. |

OTHER PUBLICATIONS

Asefi, Faucher, & Lovetri, "Surface-current measurements as data for electromagnetic imaging within metallic enclosures", Published IEEE Transactions on Microwave Theory and Techniques, 64, 4039 (2016).

Asefi, Ostadrahimi, Zakaria, Lovetri, "A 3-d dual-polarized near-field microwave imaging system", IEEE Trans. Microw. Theory Tech. (2014).

Canadian Intellectual Property Office, International Search Report for related International Application No. PCT /IB2020/056289, dated Oct. 9, 2020.

* cited by examiner

ELECTROMAGNETIC IMAGING AND INVERSION OF SIMPLE PARAMETERS IN STORAGE BINS

CROSS REFERENCE TO RELATED APPLICATIONS

This application claims the benefit of U.S. Provisional Application No. 62/892,130, filed Aug. 27, 2019, and U.S. Provisional Application No. 62/870,254, filed Jul. 3, 2019, and U.S. Provisional Application No. 62/912,337, filed Oct. 8, 2019, which are hereby incorporated by reference in their entirety.

BACKGROUND OF THE INVENTION

Field of Invention

The present disclosure is generally related to electromagnetic imaging of containers.

Description of Related Art

Imaging contents within a container is a powerful tool, especially when the interior of the container is difficult to access. In the case of grain bin monitoring, knowledge of the grain/air surface, once obtained, provides the volume of grain in the bin, which is of significant economic importance to anyone storing grain in bins. Once grain volume is known, existing methods may be used to calculate the weight of the contents of the bin. Grain is bought and sold by weight. One type of grain bin monitoring technology, referred to as electromagnetic inversion or imaging, uses radio-frequency signals, a series of antennas placed inside of a grain bin, and an inversion (or imaging) algorithm to create an image of the electrical permittivity of the contents of the bin. The electrical permittivity may be used to determine the moisture contents of the grain stored in a bin. The imaging/inversion algorithm requires that a computer model of the bin and antennas be constructed, though this model has inevitable errors. These errors (called modelling errors) require the raw radio-frequency data to be calibrated before the data can be used to generate an image.

Accordingly, electromagnetic inversion systems require that experimental data be calibrated to the computational inversion model being used, and that accurate prior information be provided to the inversion algorithm to enable higher-quality images. However, for some applications of inversion, known calibration targets cannot be easily introduced into the imaging region, and the ability to determine prior information may be limited.

BRIEF SUMMARY OF THE INVENTION

Briefly stated, one aspect of the invention is directed to a method for electromagnetic imaging of containers receives uncalibrated first data corresponding to signals of a first plurality of different frequencies associated with an antenna array residing in a container having contents. The method estimates of a second data based on a computer model and simulation of signals of a second plurality of different frequencies associated with the antenna array, the second plurality of different frequencies including a subset of the first plurality of different frequencies. The method compares magnitudes, without corresponding phase comparisons, of the first and second data at each frequency of the second plurality of different frequencies. The method updates the second data based on the comparing. The method provides information about the contents within the container based on the updated second data.

This summary is provided to introduce concepts in simplified form that are further described below in the Description of Preferred Embodiments. This summary is not intended to identify key features or essential features of the disclosed or claimed subject matter and is not intended to describe each disclosed embodiment or every implementation of the disclosed or claimed subject matter. Specifically, features disclosed herein with respect to one embodiment may be equally applicable to another. Further, this summary is not intended to be used as an aid in determining the scope of the claimed subject matter. Many other novel advantages, features, and relationships will become apparent as this description proceeds. The figures and the description that follow more particularly exemplify illustrative embodiment.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DESCRIPTION OF EXAMPLE EMBODIMENTS

Figure 1:
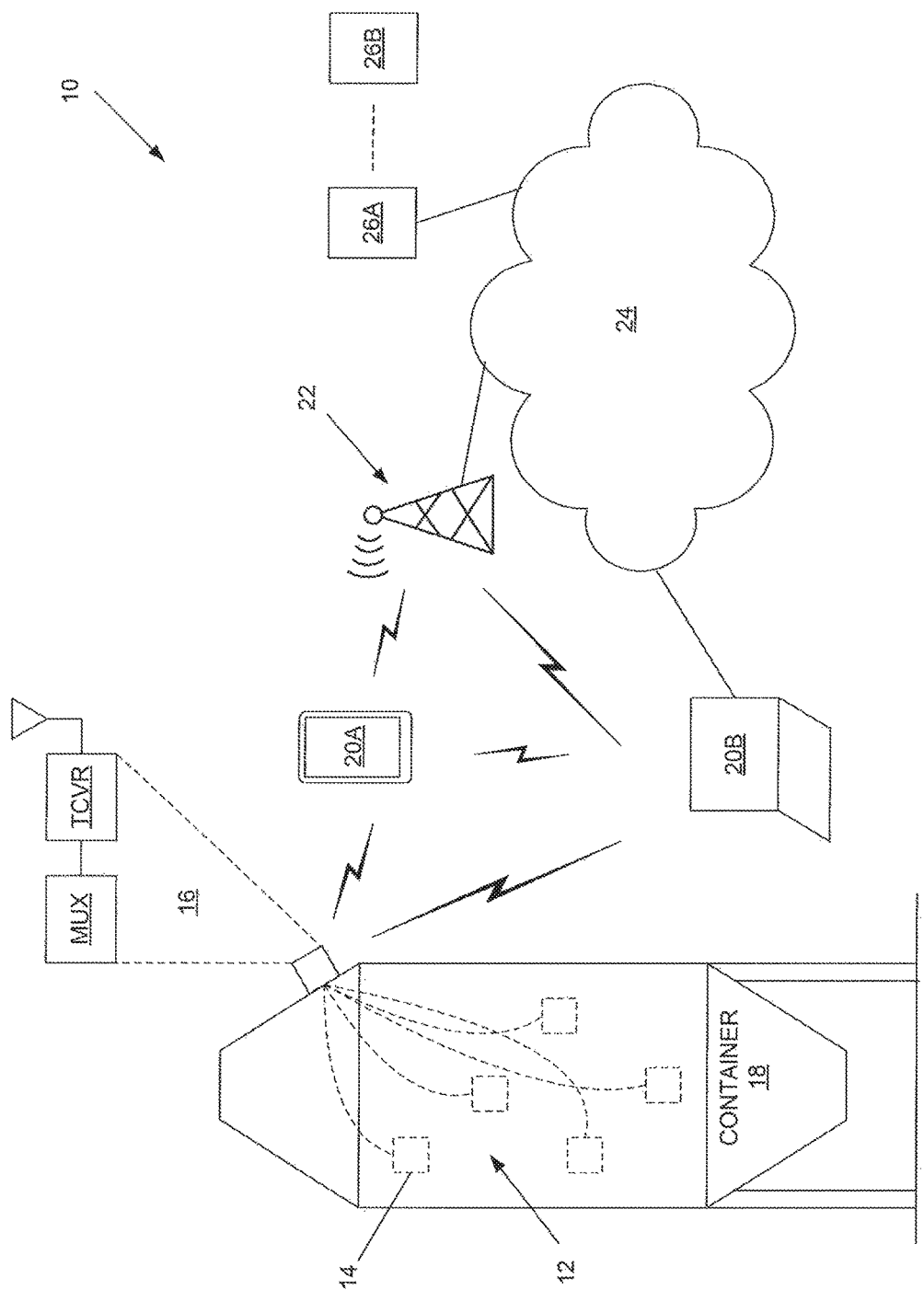
FIG. 1 is a schematic diagram that illustrates an example environment in which an embodiment of a phaseless, parametric inversion system may be implemented.

Certain embodiments of a phaseless, parametric inversion system and method that use uncalibrated data to estimate the contents within a container and derive values for the formulation of a pixel-based inversion are disclosed. In one embodiment, the phaseless, parametric inversion system compares the magnitudes of data acquired via electromagnetic signaling with the magnitudes of a computer model, without comparing the corresponding phase information, and optimizes the modeled data to derive a guess or estimate of information about the contents of the container, providing important information that can be used to determine, for the case of grain as example contents, moisture of grain, while also providing an important pre-processing step to pixel-based inversion.

Digressing briefly, current electromagnetic inversion-based grain bin monitoring techniques require that experimental data be calibrated (e.g., via physical access to the container) to the computational inversion model being used, and that accurate prior information be provided to the inversion algorithm to enable higher-quality images. Such techniques are burdensome for applications where access to the container is challenging and prior information is not sufficient or available. In contrast, certain embodiments of a phaseless, parametric inversion system do not need to introduce a target or calibration object into the imaging region, instead making use of the relatively unperturbed (e.g., unperturbed by the measurement or monitoring system) magnitude data while ignoring phase information. The magnitude data enables estimates of permittivity information (real and imaginary values) of the grain and other geometrical information pertaining to the grain volume within the container that simulates calibration data and prior information, which when further processed using a calibration equation, can be used to implement a pixel-based inversion.

Having summarized certain features of a phaseless, parametric inversion system of the present disclosure, reference will now be made in detail to the description of a phaseless, parametric inversion system as illustrated in the drawings. While a phaseless, parametric inversion system will be described in connection with these drawings, there is no intent to limit it to the embodiment or embodiments disclosed herein. For instance, in the description that follows, one focus is on grain bin monitoring. However, certain embodiments of a phaseless, parametric inversion system may be used to determine other contents of a container, including one or any combination of other materials or solids, fluids, or gases, as long as such contents reflect electromagnetic waves. Further, although the description identifies or describes specifics of one or more embodiments, such specifics are not necessarily part of every embodiment, nor are all various stated advantages necessarily associated with a single embodiment or all embodiments. On the contrary, the intent is to cover all alternatives, modifications and equivalents included within the spirit and scope of the disclosure as defined by the appended claims. Further, it should be appreciated in the context of the present disclosure that the claims are not necessarily limited to the particular embodiments set out in the description.

FIG. 1 is a schematic diagram that illustrates an example environment 10 in which an embodiment of a phaseless, parametric inversion system may be implemented. It should be appreciated by one having ordinary skill in the art in the context of the present disclosure that the environment 10 is one example among many, and that some embodiments of a phaseless, parametric inversion system may be used in environments with fewer, greater, and/or different components than those depicted in FIG. 1. The environment 10 comprises a plurality of devices that enable communication of information throughout one or more networks. The depicted environment 10 comprises an antenna array 12 comprising a plurality of antenna probes 14 and an antenna acquisition circuit 16 that is used to monitor contents within a container 18 and uplink with other devices to communicate and/or receive information. The container 18 is depicted as one type of grain storage bin (or simply, grain bin), though it should be appreciated that containers of other geometries, for the same or other contents (e.g., grain), with a different arrangement (side ports, etc.) and/or quantity of inlet and outlet ports, may be used in some embodiments. As is known, electromagnetic imaging uses active transmitters and receivers of electromagnetic radiation to obtain quantitative and qualitative images of the complex dielectric profile of an object of interest (e.g., here, the contents or grain).

As shown in FIG. 1, multiple antenna probes 14 of the antenna array 12 are mounted along the interior of the container 18 in a manner that surrounds the contents to effectively collect the scattered signal. For instance, each transmitting antenna probe is polarized to excite/collect the signals scattered by the contents. That is, each antenna probe 14 illuminates the contents while the receiving antennas probes collect the signals scattered by the contents. The antenna probes 14 are connected (via cabling) to a radio frequency (RF) switch matrix or RF multiplexor (MUX) of the antenna acquisition circuit 16, the switch/mux switching between the transmitter/receiver pairs. That is, the RF switch/mux enables each antenna probe 14 to either deliver RF energy to the container 18 or collect the RF energy from the other antenna probes 14. The switch/mux is followed by an electromagnetic transceiver (TCVR) system of the antenna acquisition circuit 16 (e.g., a vector network analyzer or VNA). The electromagnetic transceiver system generates the RF wave for illumination of the contents of the container 18 as well as receiving the measured fields by the antenna probes 14 of the antenna array 12. As the arrangement and operations of the antenna array 12 and antenna acquisition circuit 16 are known, further description is omitted here for brevity. Additional information may be found in the publications "Industrial scale electromagnetic grain bin monitoring", *Computers and Electronics in Agriculture,* 136, 210-220, Gilmore, C., Asefi, M., Paliwal, J., & LoVetri, J., (2017), "Surface-current measurements as data for electromagnetic imaging within metallic enclosures", *IEEE Transactions on Microwave Theory and Techniques,* 64, 4039, Asefi, M., Faucher, G., & LoVetri, J. (2016), and "A 3-d dual-polarized near-field microwave imaging system", *IEEE Trans. Microw. Theory Tech.*, Asefi, M., OstadRahimi, M., Zakaria, A., LoVetri, J. (2014).

Note that in some embodiments, the antenna acquisition circuit 16 may include additional circuitry, including a global navigation satellite systems (GNSS) device or triangulation-based devices, which may be used to provide location information to another device or devices within the environment 10 that remotely monitors the container 18 and associated data. The antenna acquisition circuit 16 may include suitable communication functionality to communicate with other devices of the environment.

The uncalibrated, raw data collected from the antenna acquisition circuit 16 is communicated (e.g., via uplink functionality of the antenna acquisition circuit 16) to one or more devices of the environment 10, including devices 20A and/or 20B. Communication by the antenna acquisition circuit 16 may be achieved using near field communications (NFC) functionality, Blue-tooth functionality, 802.11-based technology, satellite technology, streaming technology, including LoRa, and/or broadband technology including 3G, 4G, 5G, etc., and/or via wired communications (e.g., hybrid-fiber coaxial, optical fiber, copper, Ethernet, etc.) using TCP/IP, UDP, HTTP, DSL, among others. The devices 20A and 20B communicate with each other and/or with other devices of the environment 10 via a wireless/cellular network 22 and/or wide area network (WAN) 24, including the Internet. The wide area network 24 may include additional networks, including an Internet of Things (IoT) network, among others. Connected to the wide area network 24 is a computing system comprising one or more servers 26 (e.g., 26A, . . . 26B).

The devices 20 may be embodied as a smartphone, mobile phone, cellular phone, pager, stand-alone image capture device (e.g., camera), laptop, tablet, personal computer, workstation, among other handheld, portable, or other computing/communication devices, including communication devices having wireless communication capability, including telephony functionality. In the depicted embodiment of FIG. 1, the device 20A is illustrated as a smartphone and the device 20B is illustrated as a laptop for convenience in illustration and description, though it should be appreciated that the devices 20 may take the form of other types of devices as explained above.

The devices 20 provide (e.g., relay) the (uncalibrated, raw) data sent by the antenna acquisition circuit 16 to one or more servers 26 via one or more networks. The wireless/cellular network 22 may include the necessary infrastructure to enable wireless and/or cellular communications between the device 20 and the one or more servers 26. There are a number of different digital cellular technologies suitable for use in the wireless/cellular network 22, including: 3G, 4G, 5G GSM, CPRS, CDMAOne, CDMA2000, Evolution-Data Optimized (EV-DO), EDGE, Universal Mobile Telecommunications System (UMTS), Digital Enhanced Cordless Telecommunications (DECT), Digital AMPS (IS-136/TDMA), and Integrated Digital Enhanced Network (iDEN), among others, as well as Wireless-Fidelity (Wi-Fi), 802.11, streaming, etc., for some example wireless technologies.

The wide area network 24 may comprise one or a plurality of networks that in whole or in part comprise the Internet. The devices 20 may access the one or more server 26 via the wireless/cellular network 22, as explained above, and/or the Internet 18, which may be further enabled through access to one or more networks including PSTN (Public Switched Telephone Networks), POTS, Integrated Services Digital Network (ISDN), Ethernet, Fiber, DSL/ADSL, Wi-Fi, among others. For wireless implementations, the wireless/cellular network 22 may use wireless fidelity (Wi-Fi) to receive data converted by the devices 20 to a radio format and process (e.g., format) for communication over the Internet 18. The wireless/cellular network 22 may comprise suitable equipment that includes a modem, router, switching, etc.

The servers 26 are coupled to the wide area network 24, and in one embodiment may comprise one or more computing devices networked together, including an application server(s) and data storage. In one embodiment, the servers 26 may serve as a cloud computing environment (or other server network) configured to perform processing required to implement an embodiment of a phaseless, parametric inversion method and pixel-based inversion. When embodied as a cloud service or services, the server 26 may comprise an internal cloud, an external cloud, a private cloud, a public cloud (e.g., commercial cloud), or a hybrid cloud, which includes both on-premises and public cloud resources. For instance, a private cloud may be implemented using a variety of cloud systems including, for example, Eucalyptus Systems, VMWare vSphere®, or Microsoft® HyperV. A public cloud may include, for example, Amazon EC2®, Amazon Web Services®, Terremark®, Savvis®, or GoGrid®. Cloud-computing resources provided by these clouds may include, for example, storage resources (e.g., Storage Area Network (SAN), Network File System (NFS), and Amazon S3®), network resources (e.g., firewall, load-balancer, and proxy server), internal private resources, external private resources, secure public resources, infrastructure-as-a-services (IaaSs), platform-as-a-services (PaaSs), or software-as-a-services (SaaSs). The cloud architecture of the servers 26 may be embodied according to one of a plurality of different configurations. For instance, if configured according to MICROSOFT AZURE™, roles are provided, which are discrete scalable components built with managed code. Worker roles are for generalized development, and may perform background processing for a web role. Web roles provide a web server and listen for and respond to web requests via an HTTP (hypertext transfer protocol) or HTTPS (HTTP secure) endpoint. VM roles are instantiated according to tenant defined configurations (e.g., resources, guest operating system). Operating system and VM updates are managed by the cloud. A web role and a worker role run in a VM role, which is a virtual machine under the control of the tenant. Storage and SQL services are available to be used by the roles. As with other clouds, the hardware and software environment or platform, including scaling, load balancing, etc., are handled by the cloud.

In some embodiments, the servers 26 may be configured into multiple, logically-grouped servers (run on server devices), referred to as a server farm. The servers 26 may be geographically dispersed, administered as a single entity, or distributed among a plurality of server farms. The servers 26 within each farm may be heterogeneous. One or more of the servers 26 may operate according to one type of operating system platform (e.g., WINDOWS NT, manufactured by Microsoft Corp. of Redmond, Wash.), while one or more of the other servers 26 may operate according to another type of operating system platform (e.g., Unix or Linux). The group of servers 26 may be logically grouped as a farm that may be interconnected using a wide-area network connection or medium-area network (MAN) connection. The servers 26 may each be referred to as, and operate according to, a file server device, application server device, web server device, proxy server device, or gateway server device.

In one embodiment, one or more of the servers 26 may comprise a web server that provides a web site that can be used by users interested in the contents of the container 18 via browser software residing on a device (e.g., device 20). For instance, the web site may provide visualizations that reveal permittivity of the contents and/or geometric and/or other information about the container and/or contents (e.g., the volume geometry, such as cone angle, height of the grain along the container wall, etc.).

The functions of the servers 26 described above are for illustrative purpose only. The present disclosure is not intended to be limiting. For instance, functionality for performing the phaseless, parametric inversion and/or pixel-based inversion may be implemented at a computing device that is local to the container 18 (e.g., edge computing), or in some embodiments, such functionality may be implemented at the devices 20. In some embodiments, functionality of the phaseless, parametric inversion and/or pixel-based inversion may be implemented in different devices of the environment 10 operating according to a master-slave configuration or peer-to-peer configuration. In some embodiments, the antenna acquisition circuit 16 may bypass the devices 20 and communicate with the servers 26 via the wireless/cellular network 22 and/or the wide area network 24 using suitable processing and software residing in the antenna acquisition circuit 16.

Note that cooperation between the devices 20 (or in some embodiments, the antenna acquisition circuit 16) and the one or more servers 26 may be facilitated (or enabled) through the use of one or more application programming interfaces (APIs) that may define one or more parameters that are passed between a calling application and other software code such as an operating system, a library routine, and/or a function that provides a service, that provides data, or that performs an operation or a computation. The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer employs to access functions supporting the API. In some implementations, an API call may report to an application the capabilities of a device running the application, including input capability, output capability, processing capability, power capability, and communications capability.

An embodiment of a phaseless, parametric inversion system may include any one or a combination of the components of the environment 10. For instance, in one embodiment, the phaseless, parametric inversion system may include a single computing device (e.g., one of the servers 26 or one of the devices 20), and in some embodiments, the phaseless, parametric inversion system may comprise the antenna array 12, the antenna acquisition circuit 16, and one or more of the server 26 and/or devices 20. For purposes of illustration and convenience, implementation of an embodiment of a phaseless, parametric inversion method is described in the following as being implemented in a computing device that may be one of the servers 26, with the understanding that functionality may be implemented in other and/or additional devices.

Figure 2A:
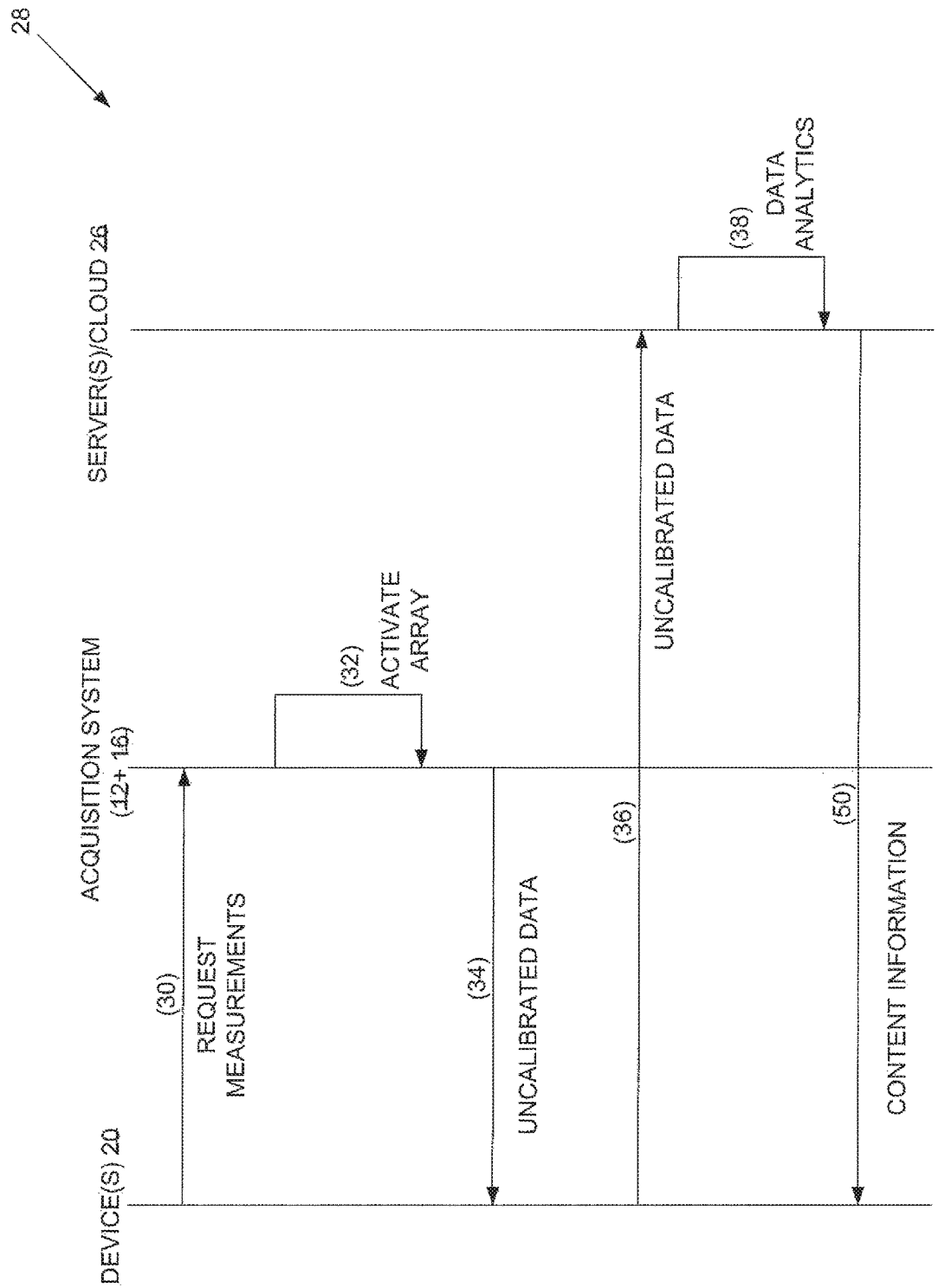
FIG. 2A is a flow diagram that illustrates an embodiment of a phaseless, parametric inversion method.

Referring now to FIG. 2A, shown is a flow diagram 28 that illustrates an embodiment of a phaseless, parametric inversion method. It should be appreciated by one having ordinary skill in the art that the components referenced in FIG. 2A as being involved in the phaseless, parametric inversion method is illustrative of one embodiment, and that in some embodiments, fewer or additional components from the environment 10 (FIG. 1) may be used. In the depicted embodiment, one of the devices 20, an acquisition system comprising the antenna array 12 and the antenna acquisition circuit 16, and a server(s) 26 are shown as the entities that enable an embodiment of the phaseless, parametric inversion method to be carried out. In (30), a user (via the device 20) requests measurements of the contents of the container 18 (FIG. 1). This request is communicated to the acquisition system. In some embodiments, the triggering of measurements may occur automatically based on a fixed time frame or based on certain conditions or based on detection of an authorized user device 20. In some embodiments, the request may trigger the communication of measurements that have already occurred. In (32), the acquisition system activates (e.g., excites) the antenna probes 14 of the antenna array 12, such that the acquisition system (via the transmission of signals and receipt of the scattered signals) collects a set of raw, uncalibrated electromagnetic data at a set of (a plurality of) discrete, sequential frequencies (e.g., 1301 frequencies from 1-1300 MHz, though not limited to this range or quantity of frequencies). In one embodiment, the uncalibrated data comprises total-field, S-parameter measurements (which are used to generate both a calibration model or information and a prior model or information as described below). As is known, S-parameters are ratios of voltage levels (e.g., due to the decay between the sending and receiving signal). Though S-parameter measurements are described, in some embodiments, other mechanisms for describing voltages on a line may be used. For instance, power may be measured directly (without the need for phase measurements), or various transforms may be used to convert S-parameter data into other parameters, including transmission parameters, impedance, admittance, etc. Since the uncalibrated S-parameter measurement is corrupted by the switching matrix and/or varying lengths (e.g., greater than five wavelengths) and/or other differences (e.g., manufacturing differences) in the cables connecting the antenna probes 14 to the antenna acquisition circuit 16, it is important that embodiments of the phaseless, parametric inversion method use only magnitude (i.e., phaseless) data as input, which is relatively unperturbed by the measurement system. In (34), the acquisition system communicates (e.g., via a wired and/or wireless communications medium) the uncalibrated (S-parameter) data to the device 20, which in turn (36) communicates the uncalibrated data to the server 26. At the server 26, data analytics are performed (38).

Through the data analytics (38), the phaseless, parametric inversion method models the calibration data and prior data to derive the information about the contents of the container 18. Digressing briefly, one problem that is solved by an embodiment of the phaseless, parametric inversion method relates to the inversion/imaging algorithms, and the calibration of the data that is collected from the bin. The current state-of-the-art inversion algorithms used in grain bins require (a) that the surface of the grain/air interface be characterized by other means, and that this surface is given to the imaging algorithms, and (b) the raw measurement data must be calibrated using measurements from data sets of known physical states in the bin. In contrast, certain embodiments of the phaseless, parametric inversion method provide a solution to generating the grain/air interface surface (and thus volume) problem via the raw, uncalibrated electromagnetic measurement. As the algorithm works on un-calibrated data, it does not require other measurements to calibrate the data. Also, the phaseless, parametric inversion method provides an estimate of the average moisture content of the contents of the bin, which is an important grain quality marker.

Figure 2B:
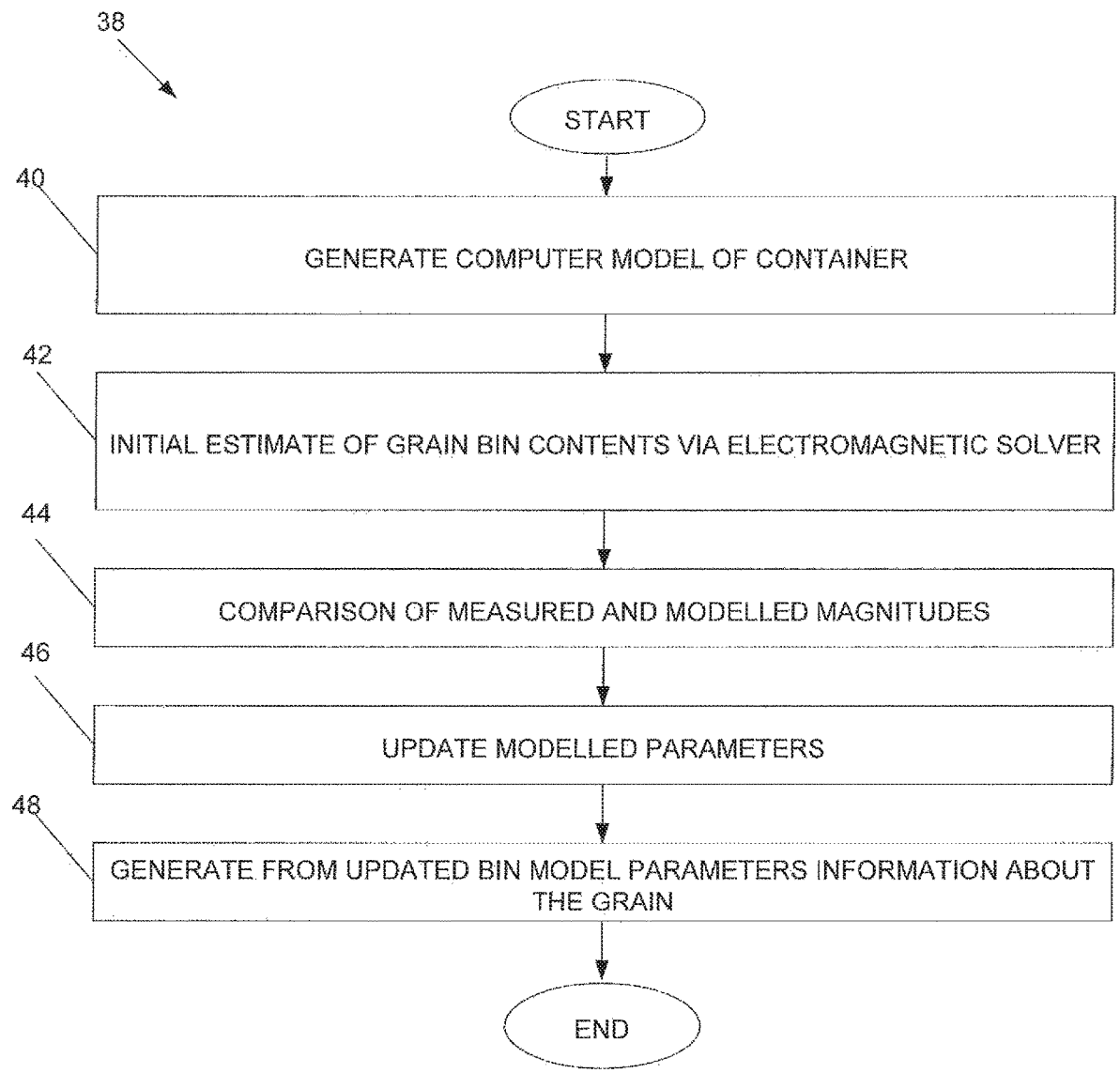
FIG. 2B is a flow diagram that illustrates an embodiment of a data analytics process of the phaseless, parametric inversion method depicted in FIG. 2A.
Figure 4:
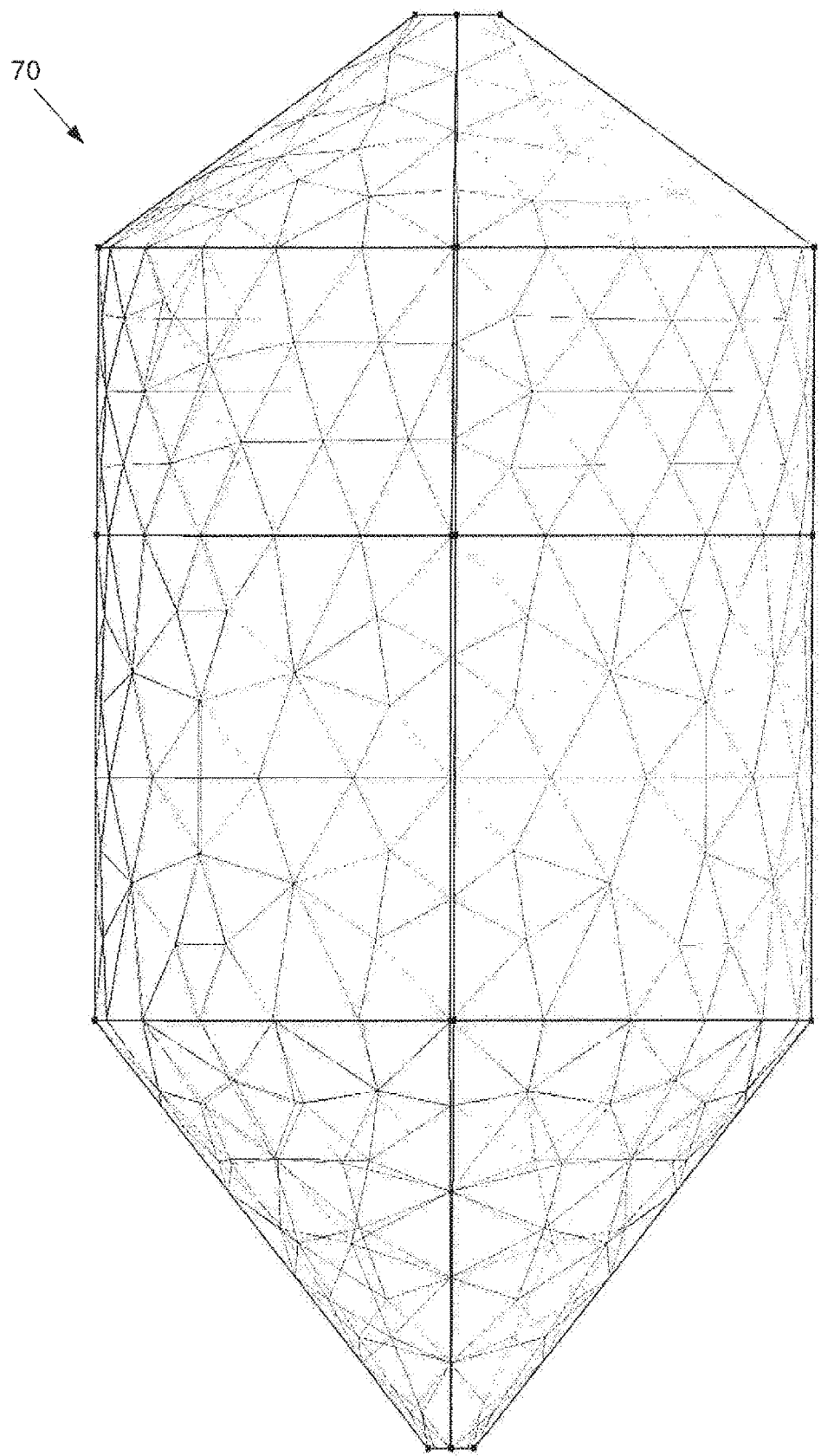
FIG. 4 is a schematic diagram that illustrates example results of a finite element model based on discretizing space inside a container using an embodiment of a phaseless, parametric inversion method.

Continuing with the data analytics (38), and referring to FIG. 2B, the phaseless, parametric inversion method generates a computer model of the container 18 (grain bin and container 18 used interchangeably herein) using a known method (e.g., a discrete mesh) (40). For instance, any one of several types of commercial, proprietary, free or open-source meshing software (e.g., GMSH) may be used to generate a 3D model of the container 18. Information about the container structure (e.g., diameter, height, etc.) may be input to the mesh software via a user interface or loaded from a file. An example visualization of the computer model is shown in FIG. 4. In one embodiment, the model includes one or more of the following estimates of the contents (grain) in the bin: grain cone angle, grain height on the bin wall, average grain permittivity (both real and imaginary parts), grain tilt angle in the bin, center location of the grain cone, or other simple geometric parameters that describe the air/grain surface. Note that the estimated parameters listed above are illustrative of a particular container geometry as indicated in FIG. 1, and that in some applications, the container may be of a different geometry or different inlet/outlet ports and/or port quantities that may engender different parameter estimates. Also, though an air/grain interface is described here for illustrative purposes, it should be appreciated by one having ordinary skill in the art that other types of interfaces (e.g., water/fuel) or different quantities of interfaces (e.g., water/fuel/air) may need to be modeled, and as such, in some embodiments, the modeled parameters may comprise geometric parameters that describe one or more interfaces between various contents of the container.

In (42), an initial estimate of the grain bin contents is made in the computer model, which has expected inaccuracies, using an electromagnetic solver. For instance, a full-wave electromagnetic solver, in conjunction with the computer model, is used to simulate the electromagnetic signals being received by the antenna array 12 (FIG. 1), at a set (or plurality) of selected frequencies. For instance, in one embodiment, the frequencies selected comprise a subset of the frequencies at which the electromagnetic signals were transmitted and collected by the acquisition system (e.g., approximately 1-10 of the frequencies collected by the transceiver system). In general, at (42), the electromagnetic solver estimates the electromagnetic fields for each simulated activation of a probe 14 of the antenna array 12 based on the 3D model of the container 18. In one embodiment, the electromagnetic solver comprises any one of a 3D finite-element method forward direct solver, a finite difference method, a method of moments, or any other computational electromagnetic forward solver.

In (44), the phaseless, parametric inversion method then considers the magnitude (e.g., voltage, and not the phase) of the physically collected data at the selected (subset) frequencies, and compares this data with the magnitude (and not the phase) of the simulated data from the computer model described above. As is known, the computer model is not completely accurate, and hence the physically collected data is compared to the model to determine changes that need to be made to the model to best approximate the physical domain. The model output and the physically collected data comprise magnitude and phase information, though the phase information from the physical domain is corrupted from various features of the physical domain (e.g., cable losses/phase shifts, switch path losses, corrupted signals due to the presence of plural antennas, receiver thermal noise, etc.). Accordingly, the phase information is removed, and a phaseless comparison is made (e.g., on the model and physically collected magnitudes) to hone in on an accurate model. For instance, in one embodiment, measured S-parameters (e.g., ratios of voltages) are compared with estimated electromagnetic field values (e.g., magnetic fields in amperes/meter), with a conversion between the two to balance the magnitudes of measured S-parameters with numerical fields according to a data scaling factor corresponding to the ratio of average values of measurements and simulated fields for each transmitter (e.g., where the denominator corresponds to the uncalibrated field measurements, and the numerator parameter corresponds to the numerical model's projected field measurements at the field probes).

Using known optimization algorithms (e.g., using derivative free or derivative based algorithms), the computer model parameters (e.g. grain cone angle) are updated in an iterative fashion based on the optimization algorithm (46). Once the new estimates are generated, (42)-(46) are repeated, unless: the error between the computer model and physical data have reached a minimum level, or the model parameters are not changing to within some tolerance, then the optimization algorithm stops. This optimization provides for a better match to the physically collected data.

Once stopped, the bin model parameters may be used to generate the volume of the grain in the bin and the average moisture content of the grain in the bin (e.g., information about the grain) (48), which is useful information that may be provided via a user interface to render feedback and/or transmitted and/or stored for later processing or review (e.g., in the way of reports).

Referring to FIG. 2A again, in (50), the content information (information about the grain) is communicated to the device 20. In some embodiments, the information is communicated for rendering and display at the device 20, or accessed from the server 26 via browser software residing on the device 20. In effect, certain embodiments of a phaseless, parametric inversion method creates a simple set of geometric parameters that describe a physical location of the grain/air interface, as well as the average electrical permittivity of the grain in the bin. Also, calibration data and prior information have been synthesized. In other words, the information about the contents is synthesized without requiring calibration data at the source.

Figure 5:
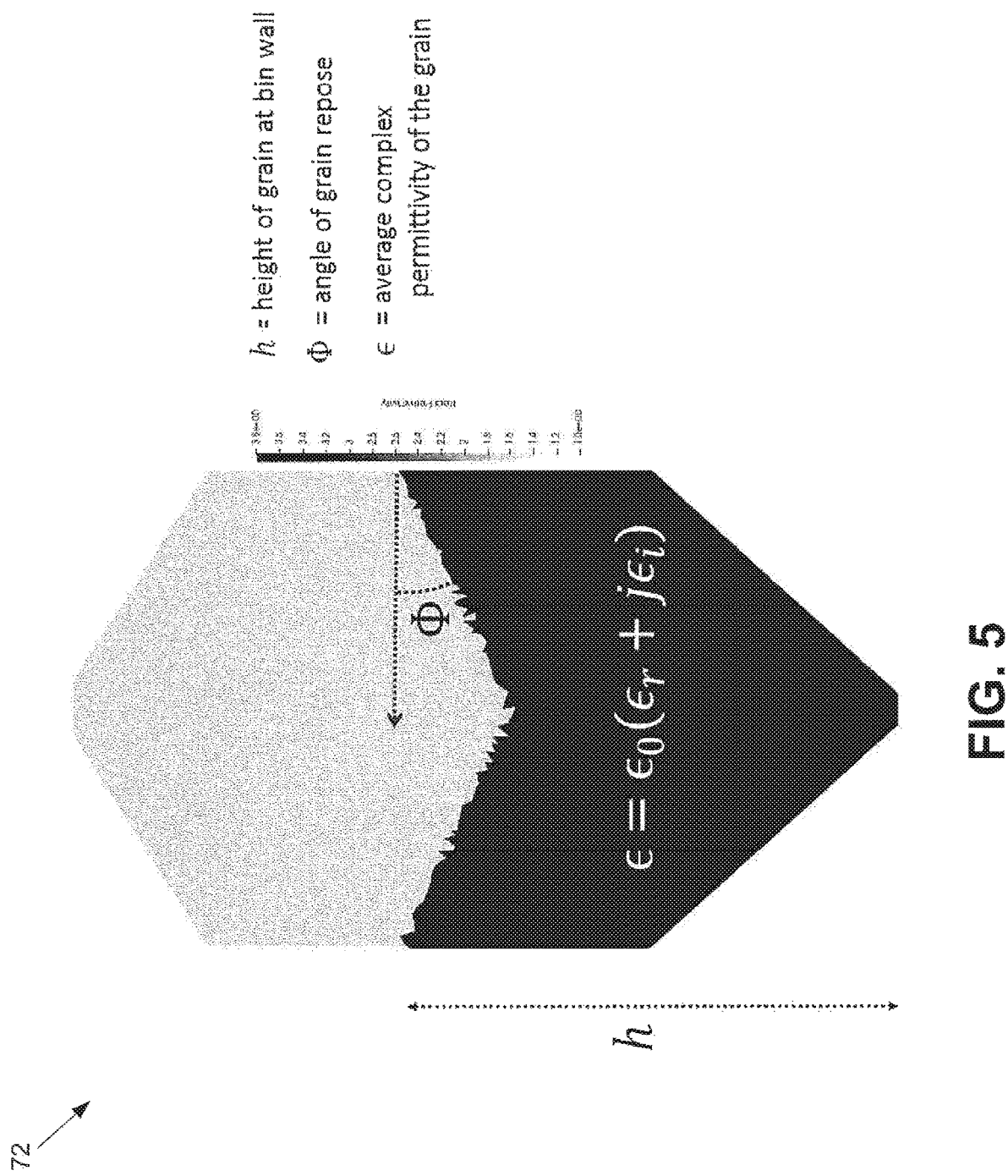
FIG. 5 is a schematic diagram that illustrates an example visualization of contents of a grain bin based on implementation of an embodiment of a phaseless, parametric inversion method.

In some embodiments, the output of the phaseless, parametric inversion method comprises the grain permittivity (e.g., imaginary and real values) and geometric information about the grain or grain volume (e.g., grain height and cone angle). In some embodiments, the output may merely comprise feedback of this information in a visualization (e.g., data presented on a screen). In some embodiments, the output comprises a more fully developed visualization of these parameters based on applying these parameters to a known, finite element mesh or other known visualization algorithm (e.g., contrast source inversion). That is, the data is used as calibration and prior information for use in a pixel-based inversion algorithm (e.g., instead of four values in this example, there are thousands or more, as shown in FIG. 5). In FIG. 5, every pixel or voxel element is ascribed a complex permittivity (real and imaginary) using an electromagnetic solver and a derivative based optimization algorithm. In other words, the phaseless, parametric inversion method comprises a pre-processing step or steps (e.g., of obtaining the prior information and calibration data) to the pixel-based inversion to derive the visualization of, for instance, the visualization shown in FIG. 5. Calibration coefficients need to be generated to format the values to that used by the pixel-based inversion algorithm, the latter also requiring phase data. In one embodiment, the following equation may be re-tasked based on estimates of calibration and prior information to generate these values (see Eqn. 1 below):

$$u_{t_x,r_x}^{sct} = \frac{u_{t_x,r_x}^{cal}}{S_{t_x,r_x}^{cal}} S_{t_x,r_x}^{unknown} - u_{t_x,r_x}^{inc}$$

-continued $$= C_{t_x,r_x} S^{unknown}_{t_x,r_x} - u^{inc}_{t_x,r_x}$$

where tx, rx, are indices for the transmit and receive pair of probes, $u^{sct}$ are the calibrated field estimates sent to the inversion code, $u^{cal}$ are fields of a known target produced by a numerical model, $s^{cal}$ are the experimental measurements for the known target, $S^{unknown}$ are experimental S-parameter measurements for the calibration target, and $u^{inc}$ are the numerical estimates for the incident field (which may be an incident field in free space, or may be an incident field for a inhomogenous background). $C_{tx,rx}$ are calibration coefficients, which modify measured data to be useful within an inversion algorithm. The calibration field and measurement $u^{cal}$ and $S^{cal}$ can be those due to any known target including a measurement of the empty imaging system. A scalar electromagnetic field model is assumed, but the principle of calibration coefficients generated from a known measurement remains the same for vector field models as well. Note that calibration coefficients are separate from the prior information. The uncalibrated data (e.g., first data) is used to generate the calibration coefficients ($C_{tx,rx}$), and estimated data (e.g., second data, based on computer model and simulation of signals) is used in Eqn. 1 to generate $u^{sct}$. The use of the information generated through the optimization of the model in a subsequent pixel based inversion is within the abilities of one having ordinary skill in the art, and hence further discussion herein is omitted.

Figure 3:
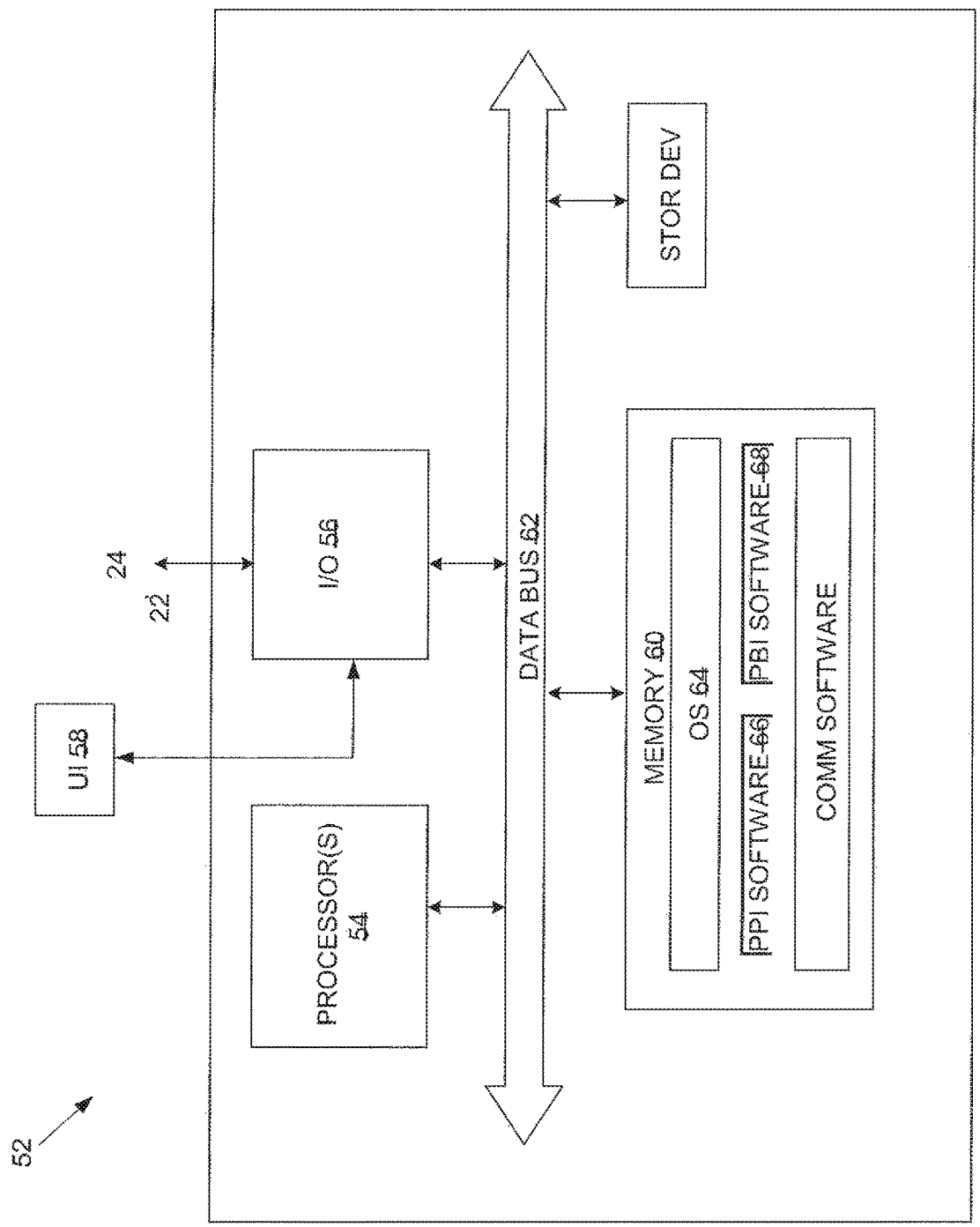
FIG. 3 is a block diagram that illustrates an example computing device of the phaseless, parametric inversion system depicted in FIG. 1.

Having described an embodiment of a phaseless, parametric inversion method and associated environment 10 in which it is used, attention is directed to FIG. 3, which illustrates an example computing device 52 used in one embodiment of the phaseless, parametric inversion system depicted in FIG. 1. In one embodiment, the computing device 52 may be one of the servers 26 or one of the devices 20. Though described as implementing certain functionality of a phaseless, parametric inversion method, in some embodiments, such functionality may be distributed among plural devices (e.g., using plural, distributed processors) that are co-located or geographically dispersed. In some embodiments, functionality of the computing device 52 may be implemented in another device, including a programmable logic controller, ASIC, FPGA, among other processing devices. It should be appreciated that certain well-known components of computers are omitted here to avoid obfuscating relevant features of computing device 52. In one embodiment, the computing device 52 comprises one or more processors, such as processor 54, input/output (I/O) interface(s) 56, a user interface 58, and memory 60, all coupled to one or more data busses, such as data bus 62. The memory 60 may include any one or a combination of volatile memory elements (e.g., random-access memory RAM, such as DRAM, and SRAM, etc.) and nonvolatile memory elements (e.g., ROM, hard drive, tape, CDROM, etc.). The memory 60 may store a native operating system, one or more native applications, emulation systems, or emulated applications for any of a variety of operating systems and/or emulated hardware platforms, emulated operating systems, etc. In the embodiment depicted in FIG. 3, the memory 60 comprises an operating system 64 and phaseless, parametric inversion (PPI) software 66 and, in some embodiments, known pixel-based inversion (PBI) software 68. In some embodiments, one or more functionality of the phaseless, parametric inversion software 66 and pixel-based inversion software 68 may be implemented in hardware. It should be appreciated by one having ordinary skill in the art that in some embodiments, additional or fewer software modules (e.g., combined functionality) may be employed in the memory 60 or additional memory. In some embodiments, a separate storage device may be coupled to the data bus 62, such as a persistent memory (e.g., optical, magnetic, and/or semiconductor memory and associated drives).

The processor 54 may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the computing device 52.

The I/O interfaces 56 provide one or more interfaces to the networks 22 and/or 24. In other words, the I/O interfaces 56 may comprise any number of interfaces for the input and output of signals (e.g., analog or digital data) for conveyance over one or more communication mediums.

The user interface (UI) 58 may be a keyboard, mouse, microphone, touch-type display device, head-set, and/or other devices that enable visualization of the contents and/or container as described above. In some embodiments, the output may include other or additional forms, including audible or on the visual side, rendering via virtual reality or augmented reality based techniques.

Note that in some embodiments, the manner of connections among two or more components may be varied. Further, the computing device 52 may have additional software and/or hardware, including communications (COMM) software that formats data according to the appropriate format to enable transmission or receipt of communications over the networks and/or wireless or wired transmission hardware (e.g., radio hardware).

The phaseless, parametric inversion software 66 comprises executable code/instructions that, when executed by the processor 54, causes the processor 54 to implement the functionality shown and described in association with phaseless, parametric inversion method depicted in FIGS. 2A-2B (and FIG. 6 described below). The pixel-based inversion software 68 comprises known algorithms for performing pixel-based inversion based on the input provided by the phaseless, parametric inversion software 66, and includes contrast source inversion or other known visualization software.

Execution of the phaseless, parametric inversion software 66 and the pixel-based inversion software 68 is implemented by the processor 54 under the management and/or control of the operating system 64. In some embodiments, the operating system 64 may be omitted. In some embodiments, functionality of the phaseless, parametric inversion software 66 and the pixel-based inversion software 68 may be distributed among plural computing devices (and hence, plural processors).

When certain embodiments of the computing device 52 are implemented at least in part with software (including firmware), as depicted in FIG. 3, it should be noted that the software can be stored on a variety of non-transitory computer-readable medium (including memory 60) for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device 52 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

FIG. 4 is a schematic diagram 70 that illustrates example results of a finite element model, described above, based on discretizing space inside a container using an embodiment of a phaseless, parametric inversion method.

FIG. 5 is a schematic diagram 72 that illustrates an example visualization of contents of a grain bin based on implementation of an embodiment of a phaseless, parametric inversion method. As shown, the visualization may include parameter values describing permittivity and geometric information about the contents, including the height of the grain along the container wall, the angle of grain repose, and the average complex permittivity of the grain. In some embodiments, the rendering of the color of the grain may be indicative of average grain moisture content, among other parameters.

Figure 6:
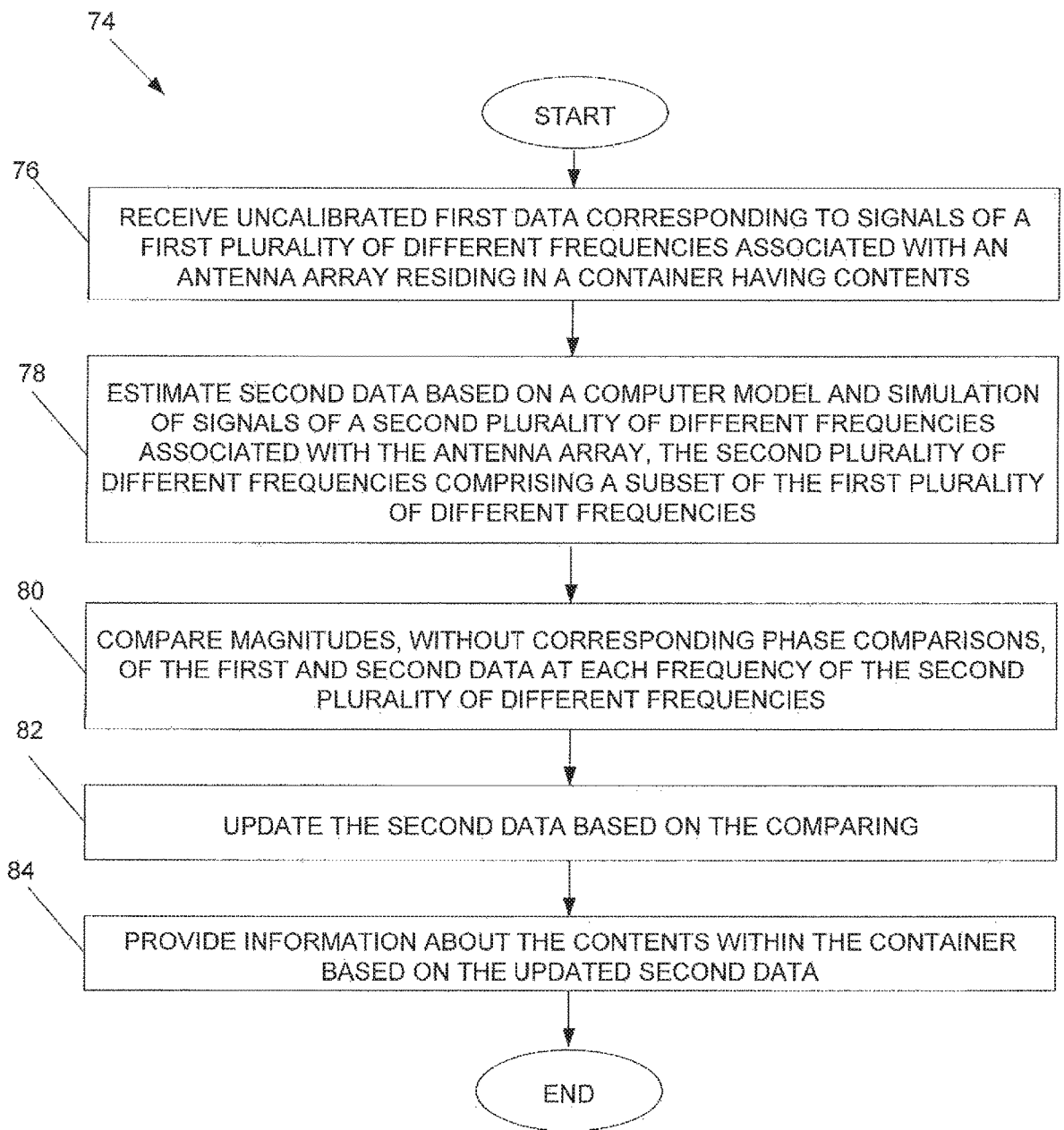
FIG. 6 is a flow diagram that illustrates an embodiment of an example phaseless, parametric inversion method.

Having described certain embodiments of a phaseless, parametric inversion system, it should be appreciated within the context of the present disclosure that one embodiment of a phaseless, parametric inversion method, denoted as method 74 and illustrated in FIG. 6, and implemented using one or more processors (e.g., of a computing device or plural computing devices), comprises receiving uncalibrated first data corresponding to signals of a first plurality of different frequencies associated with an antenna array residing in a container having contents (76); estimating second data based on a computer model and simulation of signals of a second plurality of different frequencies associated with the antenna array, the second plurality of different frequencies comprising a subset of the first plurality of different frequencies (78); comparing magnitudes, without corresponding phase comparisons, of the first and second data at each frequency of the second plurality of different frequencies (80); updating the second data based on the comparing (82); and providing information about the contents within the container based on the updated second data (84).

Any process descriptions or blocks in flow diagrams should be understood as representing logic and/or steps in a process, and alternate implementations are included within the scope of the embodiments in which functions may be executed out of order from that shown or discussed, including substantially concurrently, or with additional steps (or fewer steps), depending on the functionality involved, as would be understood by those reasonably skilled in the art of the present disclosure.

One advantage of an embodiment of a phaseless, parametric inversion method is that it uses un-calibrated electromagnetic data collected by the transceiver/antenna array at a small number (e.g., 1-10) of frequencies to generate the volume of the grain in the bin. This does not require any prior information of the state of the grain in the bin. All other methods of imaging with a transceiver/antenna array require calibration and/or prior information about the bin contents. Further, the model of the grain bin produced by an embodiment of a phaseless, parametric inversion method may be used in the more general imaging procedure as a method of calibrating the data.

Figure 7:
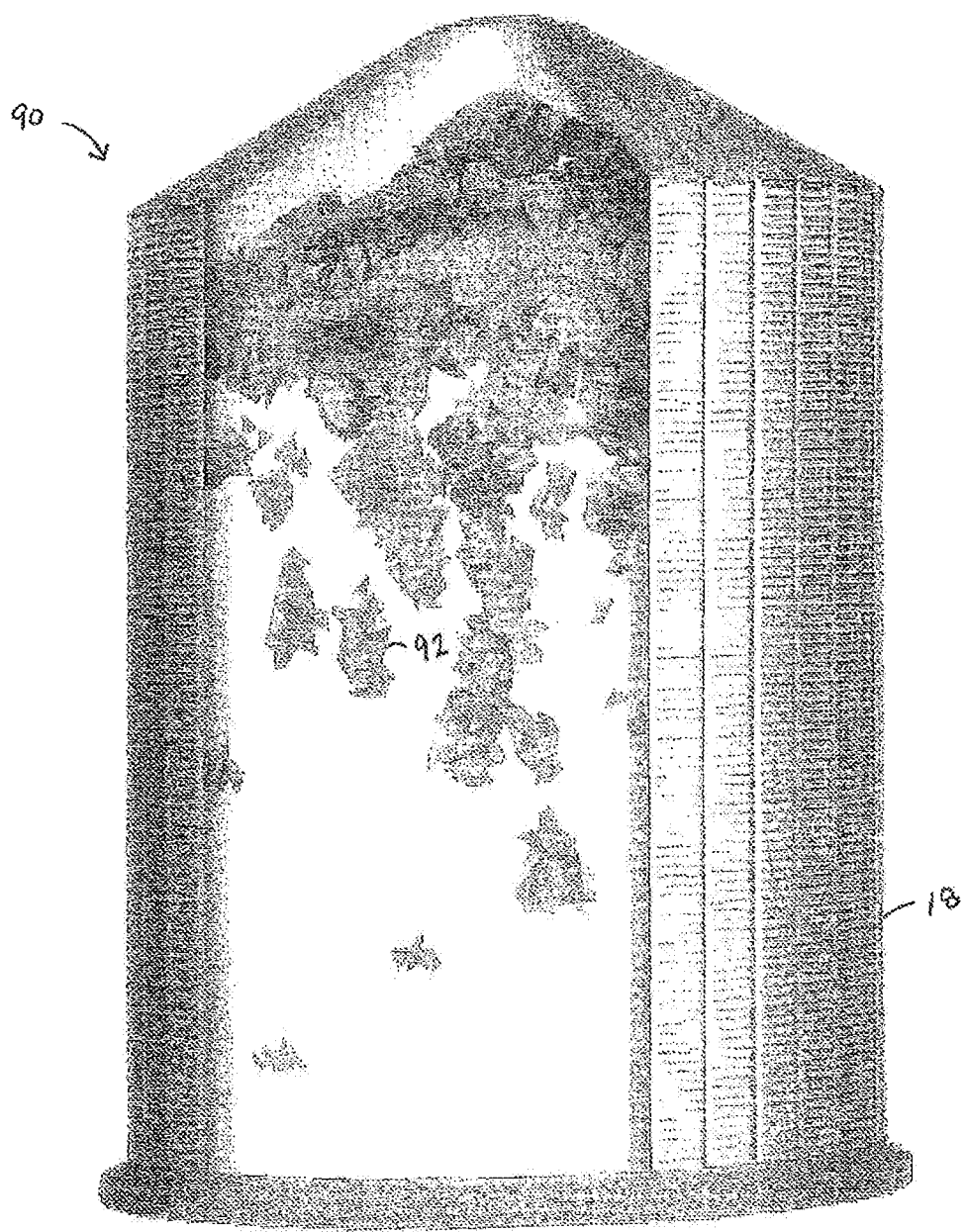
FIG. 7 is display map that illustrates moisture content of individual bushels of grain and its location with the grain mass within the container generated using the phaseless, parametric inversion system.

Referring now to FIG. 7, in one embodiment a three dimensional moisture map 90 is generated using the data acquisition hardware attached to the container 18 that measures the internal bin response to internal electromagnetic interrogation and the software algorithms that convert at least a subset of the measured data to an image of the contents container 18. From the map 90, an operator can see the moisture content of individual bushels 92 or pockets of grain and its location with the grain mass within the container 18. Bushels 92 are displayed on the map using different colors or shades based on the moisture content determined by the imaging process.

Figure 8:
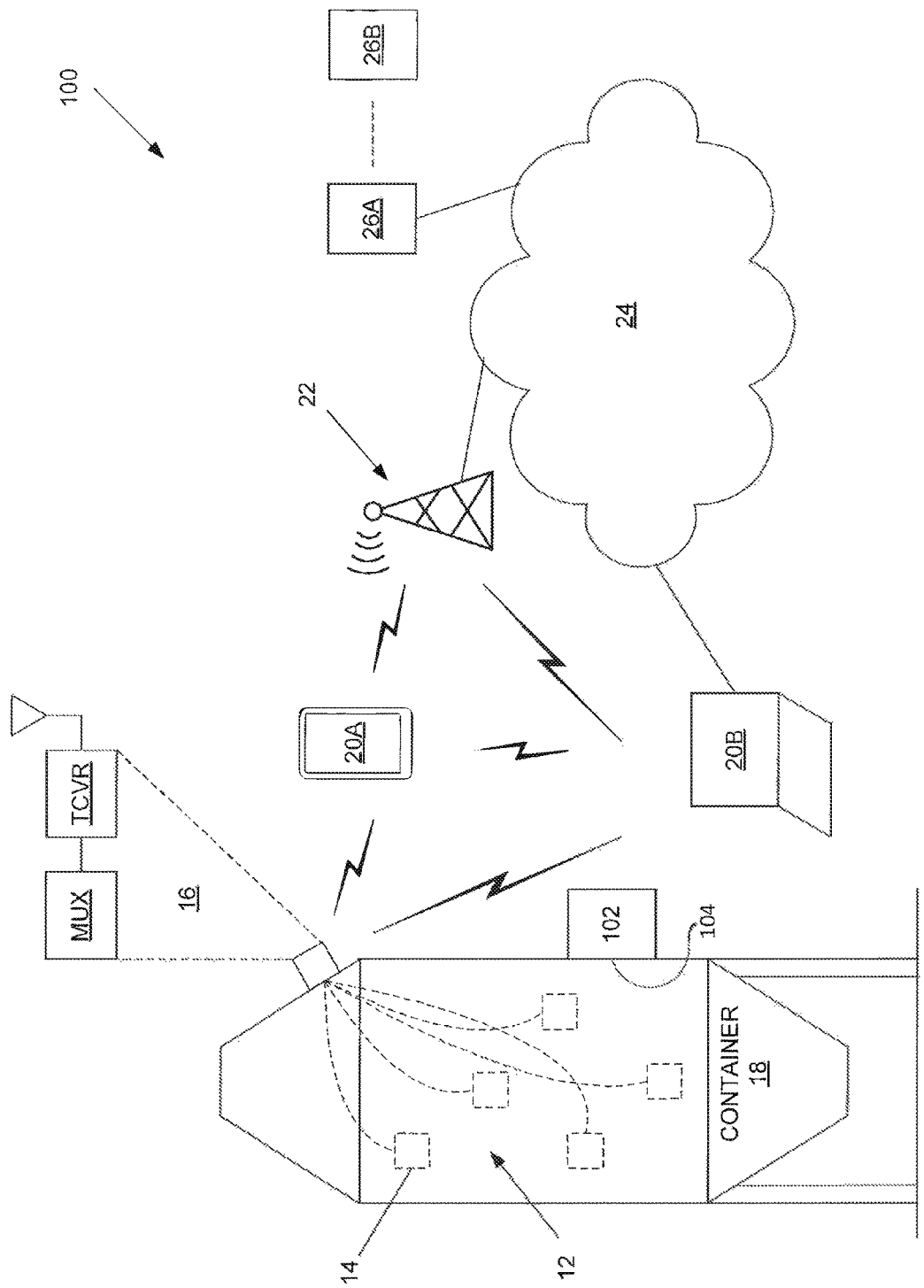
FIG. 8 is a schematic diagram of another example environment in which detection and localization of human entry or other hazards within a container.
Figure 9:
FIG. 9 is view of a human phantom target partially buried in a grain container to be detected and localized.

In another embodiment, FIG. 8 shows an electromagnetic environment system 100 similar to the electromagnetic environment 10 described above and where like numbers are used for like components of the environment. The environment 100 includes the antenna array 12 with the plurality of antenna probes 14 and antenna acquisition circuit 16 used to monitor contents within the container 18 is used for the detection and localization of hazards within the container 18. For example, the antenna array 12 can be used to detect and localize human entry into the container 18.

A real-time bin entry door monitor 102, such as an electronic switch or other known detector, triggers whenever a bin access door 104 is opened and/or entry is possible into the container 18. This information is communicated to the central hub for processing via infrastructure as described above.

The system 100 is setup to periodically collect broadband electromagnetic interrogation date of the bin contents from 10-1300 MHz using the hardware system. Desirably, periodicity of the data collection coincides with the scale of human activities or monitoring urgency (i.e., minutes) as opposed to grain storage timelines (i.e., days).

Figure 10:
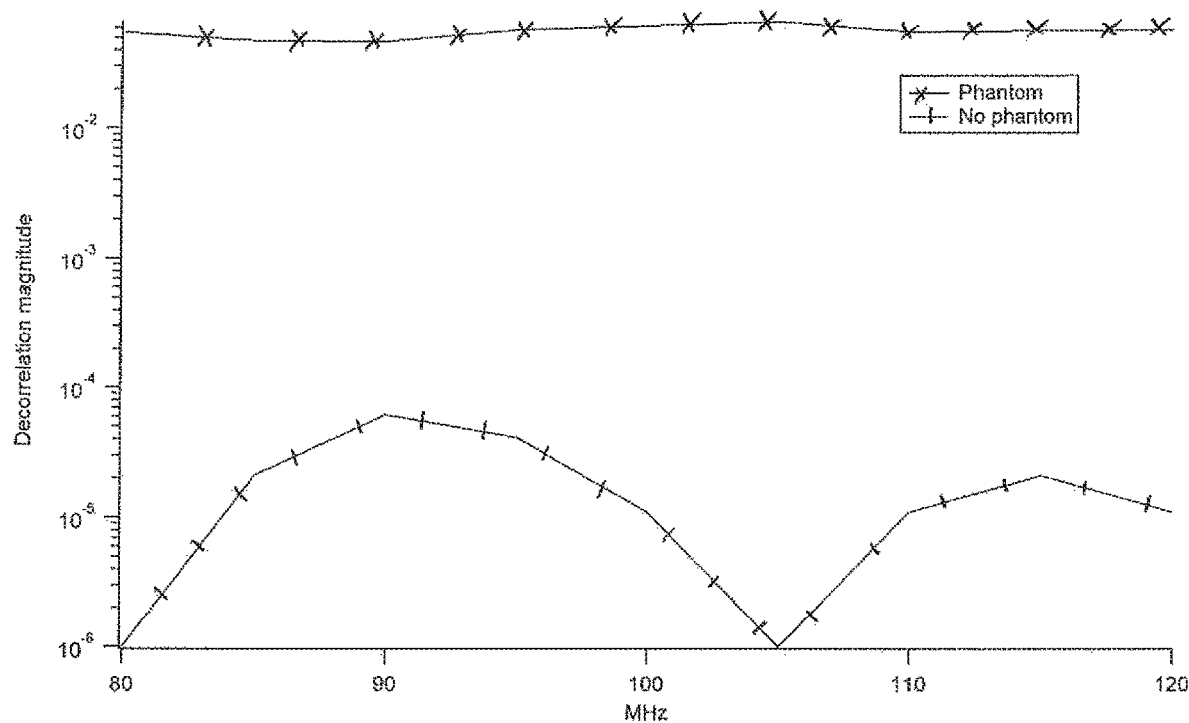
FIG. 10 is a chart with raw signal analysis showing a difference in correlation coefficients between human phantom target and no-phantom target (i.e. just grain) data sets.

In the event of an entry door open event is detected by the door monitor 102, the system 100 continuously compares broadband data to a baseline data collected before the entry door hatch event occurred. Differences in data indicate the possibility of human entry as a human is a very strong electromagnetic scatterer compared to grain and would perturb the field pattern in the container 18. FIG. 10 displays an example of the raw signal analysis that shows a clear difference between the presence and non-presence of the human phantom in the container 18.

Figure 11A:
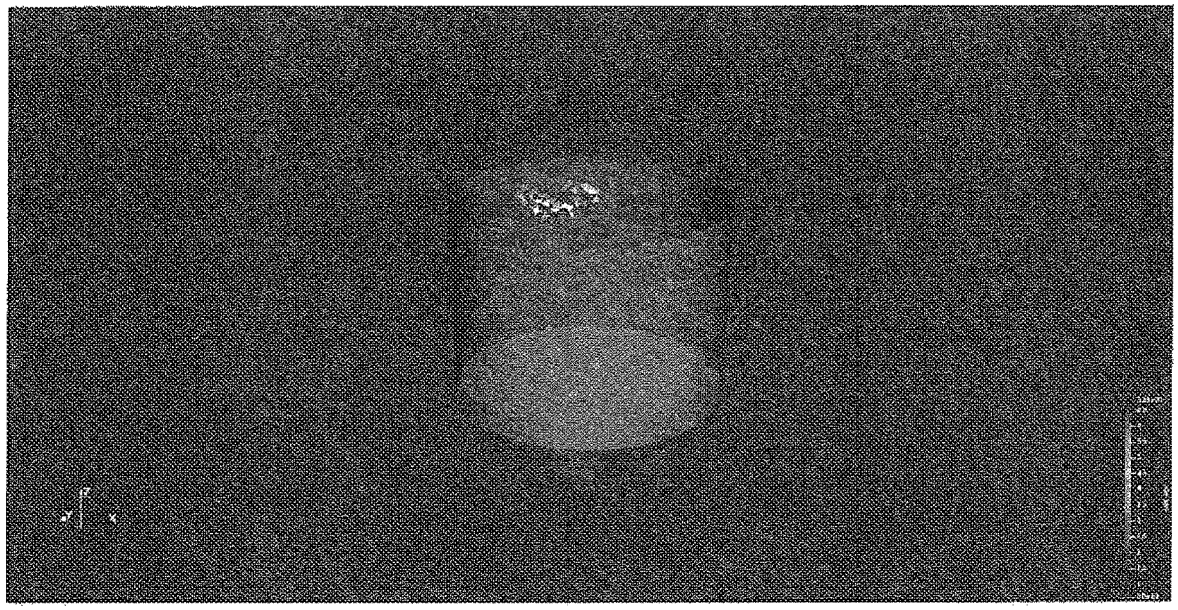
FIG. 11A is a display of single iteration imaging for detecting a human-phantom in a container.
Figure 11B:
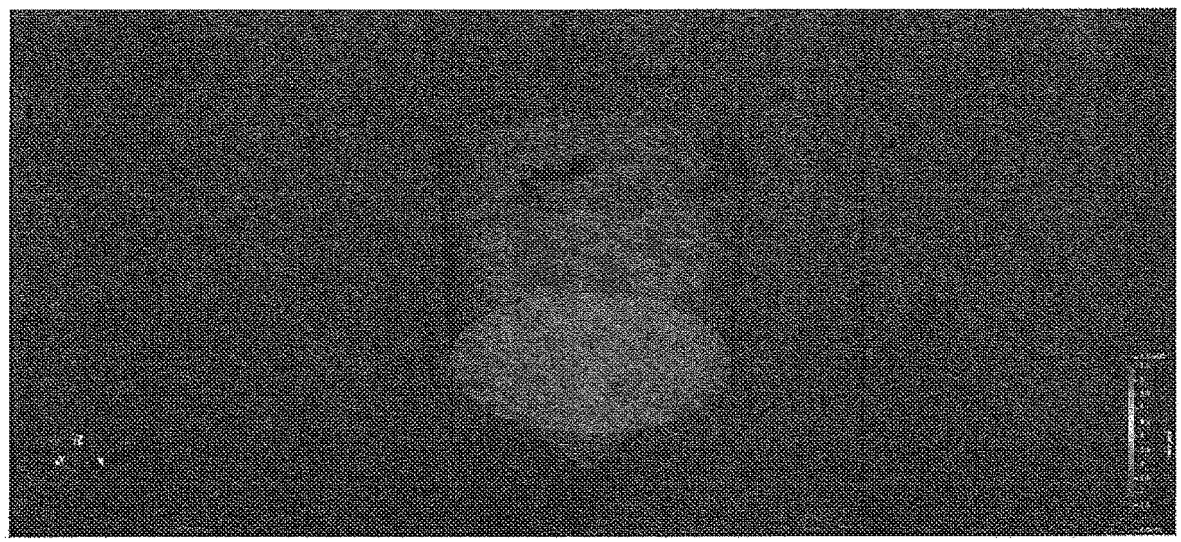
FIG. 11B is a display of full-instance imaging for detecting a human-phantom in a container.

In one embodiment, a single iteration (such as a Born Approximation or similar) of an electromagnetic imaging algorithm is used to determine if a large human scatterer is present in the container. FIG. 11A displays experimental results detecting a simulated human (e.g., water-based target) in a 2500 bushel test container. The solid voxels in the image of FIG. 11A are at the location of the human phantom target, and the image is produced much more rapidly than the full image shown in FIG. 10. For example, it is desirable that the image generation using the single iteration of an electromagnetic imaging algorithm takes approximately 5 minutes. Depending on established protocols/situational requirements, the tracking of the target location is continued using simple Born Approximation imaging, or the system 100 could run a full instance of the imaging algorithm to improve the image. FIG. 11B displays an experimental result of the full-instance imaging for detecting a human-phantom in a 2500 bushel bin. The solid voxels in the image of FIG.

11B are at the location of the human phantom. The quality of the image is improved over the rapid case single iteration image of FIG. 11A, but the full-instance imaging takes substantially longer, for example, approximately one hour to generate.

Throughout the sequence of events presented and data collected, alerts may be triggered via the software platform, and sent to designated emergency contacts and/or first responders. The escalation path for alerting will be determined by the information collected as details of the intrusion become available, as well as through end user interaction (or lack thereof). In the event of a complete engulfment, the invention also provides the ability locate and aid in the recovery of the body from within the stored grain.

While imaging algorithms as a whole take time to run, the invention can make use of any efforts to improve the imaging algorithm efficiency, including: i) machine learning algorithms trained solely to determine large ellipsoid human-property targets in a grain bin (or similar) and ii) compressive sensing algorithms that exploit sparsity in looking for single human-shaped targets in a bin.

When no entry alerts are present, these same algorithms are periodically (on a grain storage scale, i.e., days) executed to look for voids in the grain to address if hazards exist or conditions for hazards are developing in the container 18.

Figure 12:
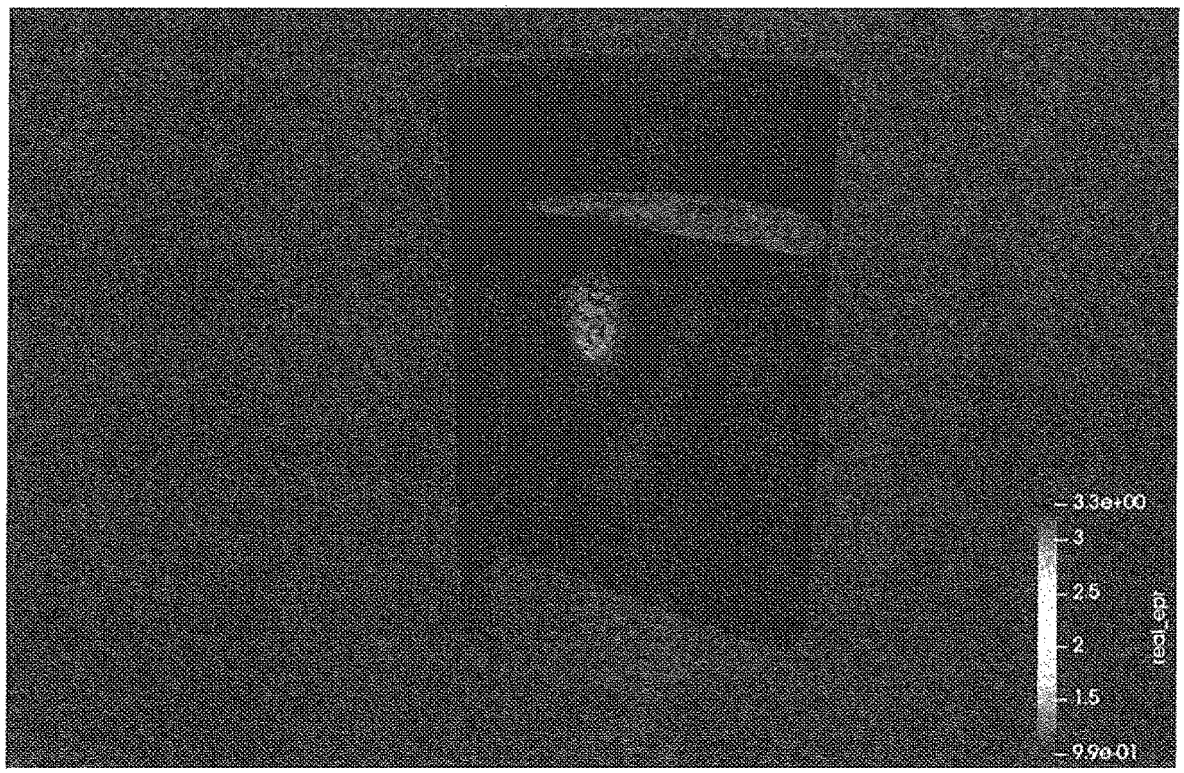
FIG. 12 is a display of full-instance imaging for detecting a hazard such as an air void in a container Corresponding reference characters indicate corresponding parts throughout the views of the drawings.

This overall framework, made possible by re-tooling monitoring capabilities for human entry detection and localization provides significant flexibility in detection and localization capabilities from near instantaneous potential entry detection to complete target classification and localization, depending on the safety and situational requirements that may arise. For example, FIG. 12 shows the detection of an air void in a container 18.

S19It should be emphasized that the above-described embodiments of the present disclosure are merely possible examples of implementations, merely set forth for a clear understanding of the principles of the disclosure. Many variations and modifications may be made to the above-described embodiment(s) of the disclosure without departing substantially from the scope of the disclosure. All such modifications and variations are intended to be included herein within the scope of this disclosure and protected by the following claims.

The invention claimed is:

1. A method for electromagnetic imaging of containers, comprising:
   in one or more processors:
      receiving uncalibrated first data corresponding to signals of a first plurality of different frequencies associated with an antenna array residing in a container having contents;
      estimating second data based on a computer model and simulation of signals of a second plurality of different frequencies associated with the antenna array, the second plurality of different frequencies comprising a subset of the first plurality of different frequencies;
      comparing magnitudes, without corresponding phase comparisons, of the first and second data at each frequency of the second plurality of different frequencies;
      updating the second data based on the comparing; and
      providing information about the contents within the container based on the updated second data.

2. The method of claim 1, wherein receiving comprises receiving uncalibrated S-parameter measurement data.

3. The method of claim 1, wherein estimating comprises estimating one or more parameters of the contents in the container.

4. The method of claim 3, wherein the one or more parameters comprises one or more geometric parameters that describe one or more interfaces between various contents of the container.

5. The method of claim 3, wherein the contents comprise grain, and wherein the one or more parameters comprises one or any combination of grain permittivity or geometric parameters corresponding to grain volume.

6. The method of claim 1, wherein the estimating comprises using an electromagnetic solver with the computer model to simulate the signals associated with the second data expected to be received at the antenna array.

7. The method of claim 6, wherein the electromagnetic solver comprises any one of a 3D finite-element method forward direct solver, a finite difference method, a method of moments, or computational electromagnetic forward solver.

8. The method of claim 1, wherein updating comprises using an optimization algorithm iteratively.

9. The method of claim 8, wherein the updating is repeated until one of the comparing results in a minimum value or changes in the second data are lower than a threshold level.

10. The method of claim 1, wherein the updated second data comprises permittivity information and geometry information corresponding to contents within the container.

11. The method of claim 1, wherein the contents comprises grain, and wherein the updated second data comprises real and imaginary permittivity of the grain, grain height, and cone angle.

12. The method of claim 1, wherein providing comprises providing a visualization of the container and geometries of the contents within the container.

13. The method of claim 1, wherein providing comprises providing moisture content of the contents within the container.

14. The method of claim 1, wherein providing further comprises:
   using the first data to derive calibration coefficients; and
   performing pixel-based inversion based on the calibration coefficients and prior information.

* * * * *